United States Patent [19]
Weichert et al.

[11] Patent Number: 5,856,574
[45] Date of Patent: Jan. 5, 1999

[54] ORTHO-SUBSITUTED BENZOYLGUANIDINES, PROCESS FOR THEIR PREPARATION, THEIR USE AS A MEDICAMENT OR DIAGNOSTIC, AND MEDICAMENT CONTAINING THEM

[75] Inventors: Andreas Weichert, Egelsbach; Joachim Brendel, Bad Vilbel; Heinz-Werner Kleemann, Bischofsheim; Hans Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 804,023

[22] Filed: Feb. 21, 1997

[30] Foreign Application Priority Data

Feb. 22, 1996 [DE] Germany .................. 196 06 509.7

[51] Int. Cl.⁶ .................................................. C07C 233/00
[52] U.S. Cl. ........................................... 564/183; 514/617
[58] Field of Search ............................. 514/617; 564/183

[56] References Cited

FOREIGN PATENT DOCUMENTS

| | | |
|---|---|---|
| 2-7150794 | 8/1994 | Australia . |
| 9455229 | 8/1994 | Australia . |
| 668265B | 3/1995 | Australia . |
| 9471507 | 3/1995 | Australia . |
| 52252/96 | 11/1996 | Australia . |
| 5225296 | 11/1996 | Australia . |
| 9652252 | 11/1996 | Australia . |
| 0 612 723 | 8/1994 | European Pat. Off. . |
| 0 640 588 | 3/1995 | European Pat. Off. . |
| 0 743 301 | 11/1996 | European Pat. Off. . |

*Primary Examiner*—Raymond Henley, III
*Assistant Examiner*—Dwayne C. Jones
*Attorney, Agent, or Firm*—Finnegan, Henderson, Farabow, Garrett & Dunner, L.L.P.

[57] ABSTRACT

Ortho-substituted benzoylguanidines, process for their preparation, their use as a medicament or diagnostic, and medicament containing them Ortho-substituted benzoylguanidines of the formula I

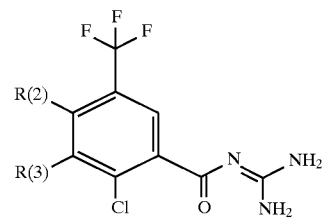

in which R(2) and R(3) have the meanings given in the claims, are suitable, as antiarrhythmic pharmaceuticals having a cardioprotective component, for the prophylaxis and treatment of infarction and for the treatment of angina pectoris. They also inhibit, in a preventive manner, the pathophysiological processes associated with the development of ischemically induced damage, in particular in association with the triggering of ischemically induced cardiac arrhythmias.

18 Claims, No Drawings

ORTHO-SUBSITUTED BENZOYLGUANIDINES, PROCESS FOR THEIR PREPARATION, THEIR USE AS A MEDICAMENT OR DIAGNOSTIC, AND MEDICAMENT CONTAINING THEM

DESCRIPTION

Ortho-substituted benzoylguanidines, process for their preparation, their use as a medicament or diagnostic, and medicament containing them.

The invention relates to ortho-substituted benzoylguanidines of the formula I

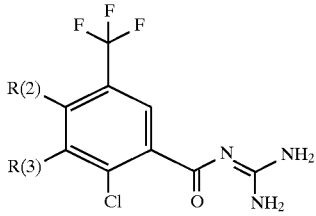

in which:
R(2) and R(3) are,
independently of each other, hydrogen, Cl, Br, 1, $(C_1-C_8)$-alkyl, $(C_3-C_8)$-cycloalkyl or —OR(5);
R(5) is $(C_1-C_8)$-alkyl or —$C_dH_{2d}$—$(C_3-C_8)$-cycloalkyl;
d is zero, 1 or 2;
where one of the two substituents R(2) and R(3) is always hydrogen but both substituents R(2) and R(3) are not simultaneously hydrogen, and the pharmaceutically tolerated salts thereof.

Preference is given to compounds of the formula I in which:
R(2) and R(3) are,
independently of each other, hydrogen, Cl, Br, 1, $(C_1-C_8)$-alkyl, $(C_3-C_8)$-cycloalkyl or —OR(5);
R(5) is $(C_1-C_8)$-alkyl;
and the pharmaceutically tolerated salts thereof.

Very particular preference is given to the following compounds: 2-chloro4-methoxy-5-trifluoromethylbenzoylguanidine hydrochloride, 2-chloro-3-methoxy-5-trifluoromethylbenzoylguanidine hydrochloride, 2-chloro-3-iodo-5-trifluoromethylbenzoylguanidine hydrochloride, 2-chloro-3-methyl-5-trifluoromethylbenzoylguanidine hydrochloride, 2-chloro-3-n-propyl-5-trifluoromethylbenzoylguanidine hydrochloride, 2-chloro-3-isopropyl-5-trifluoromethylbenzoylguanidine hydrochloride, 2-chloro-3-tert-butyl-5-trifluoromethylbenzoylguanidine hydrochloride, 2-chloro-3-cyclopentyl-5-trifluoromethylbenzoylguanidine hydrochloride, 2-chloro4-methyl-5-trifluoromethylbenzoylguanidine hydrochloride, 2-chloro4-n-propyl-5-trifluoromethylbenzoylguanidine hydrochloride, 2-chloro4-isopropyl-5-trifluoromethylbenzoylguanidine hydrochloride, 2-chloro-4-tert-butyl-5-trifluoromethylbenzoylguanidine hydrochloride and 2-chloro4-cyclopentyl-5-trifluoromethylbenzoylguanidine hydrochloride.

If one of the substituents R(2) or R(3) contains one or more centers of asymmetry, these can then be either in the S or the R configuration. The compounds may be present as optical isomers, as diastereomers, as racemates or as mixtures thereof.

The indicated alkyl radicals can be straight-chain or branched.

The invention furthermore relates to a process for preparing the compound I, which comprises reacting compounds of the formula II

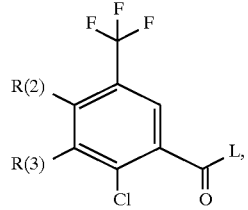

in which R(2) and R(3) have the given meaning and L is a leaving group which can readily be substituted nucleophilically, with guanidine.

The activated acid derivatives of the formula II, in which L is an alkoxy group, preferably a methoxy group, a phenoxy group, a phenylthio group, a methylthio group or a 2-pyridylthio group, or a nitrogen heterocycle, preferably 1-imidazolyl, are advantageously obtained, in a manner known per se, from the underlying carbonyl chlorides (formula II, L=Cl), which can, for their part, in turn be prepared in a manner known per se from the underlying carboxylic acids (formula II, L=OH), for example using thionyl chloride.

In addition to the carbonyl chlorides of the formula II (L=Cl), other activated acid derivatives of the formula II can also be prepared in a manner known per se directly from the underlying benzoic acid derivatives (formula II, L=OH), for example the methyl esters of the formula II, in which $L=OCH_3$, by treating with gaseous HCl in methanol, the imidazolides of the formula II by treating with carbonyl diimidazole [L=1-imidazolyl, Staab, Angew. Chem. Int. Ed. Engl. 1,351–367 (1962)], the mixed anhydrides II with $Cl-COOC_2H_5$ or tosyl chloride in the presence of triethylamine in an inert solvent, while there is also the activation of benzoic acids with dicyclohexylcarbodiimide (DCC) or with O-[(cyano(ethoxycarbonyl)methylen)amino]-1,1,3,3-tetramethyluronium tetrafluoroborate ("TOTU")[Weiss and Krommer, Chemiker Zeitung 98, 817 (1974)]. A series of suitable methods for preparing activated carboxylic acid derivatives of the formula II is described, with citation of the source literature, in J. March, Advanced Organic Chemistry, Third Edition (John Wiley & Sons, 1985), p. 350.

An activated carboxylic acid derivative of the formula II is reacted with guanidine, in a manner known per se, in a protic or aprotic, polar but inert organic solvent. In this context, methanol, isopropanol or THF, at a temperature of from 20° C. up to the boiling temperature of these solvents, have proved to be of value when reacting methyl benzoates (II, L=OMe) with guanidine. Most of the reactions of compounds II with salt-free guanidine were advantageously carried out in aprotic, inert solvents such as THF, dimethoxyethane or dioxane. However, when a base, for example NaOH, is used, water can also be employed as a solvent when reacting II with guanidine.

When L=Cl, the process is advantageously carried out in the presence of an added acid-capturing agent, for example in the form of excess guanidine, for the purpose of removing the hydrohalic acid.

Some of the underlying benzoic acid derivatives of the formula II are known and described in the literature. The unknown compounds of the formula II may be prepared using methods which are known from the literature. The resulting benzoic acids are converted into novel compounds I using one of the above described process variants.

The introduction of some substituents into the 3 and 4 positions is achieved using methods, which are known from the literature, for the palladium-mediated cross-coupling of aryl halides or aryl triflates with, for example, organostannanes, organoboronic acids or organoboranes, or organocopper compounds or organozinc compounds.

In general, benzoylguanidines I are weak bases and are able to bind acid with the formation of salts. Suitable acid addition salts are salts of all pharmacologically tolerated acids, for example halides, in particular hydrochlorides, lactates, sulfates, citrates, tartrates, acetates, phosphates, methylsulfonates and p-toluenesulfonates.

The compounds I are substituted acylguanidines.

Compounds of a similar constitution, which are also able to carry a $CF_3$ group, in addition to a large number of other R(1) substituents, in the 5 position and to carry a Cl atom, in addition to a large number of substituents, in the 2 position, are disclosed in European Laid-open Specification 640 588 A 1. However, it was not possible to predict that precisely these compounds, having a trifluoromethyl group and a chlorine atom as substituents, would display an outstanding effect.

It was surprising that, in addition to exhibiting very good antiarrhythmic properties, the novel compounds not only fail to exhibit any undesirable and disadvantageous salidiuretic properties but also simultaneously exhibit a particularly favorable, relatively low half life, which is often undesirably long in the case of known compounds. The novel compounds are furthermore notable for their good bioavailability, as is demonstrated by the in-vivo values.

As a consequence of their pharmacological properties, the present compounds, like the known compounds, are outstandingly suitable, as antiarrhythmic pharmaceuticals having a cardioprotective component, for the prophylaxis and treatment of infarction and for the treatment of angina pectoris, in association with which they also inhibit or markedly diminish, in a preventive manner, the pathophysiological processes associated with the development of ischemically induced damage, in particular in association with the triggering of ischemically induced cardiac arrhythmias. On account of their protective effects against pathological hypoxic and ischemic situations, the novel compounds of the formula I can be used, as a consequence of the inhibition of the cellular $Na^+/H^+$-exchange mechanism, as pharmaceuticals for treating all acute or chronic damage which is provoked by ischemia, or diseases which are primarily or secondarily induced thereby. This relates to their use as pharmaceuticals for surgical interventions, for example in association with organ transplantations, with it being possible for the compounds to be used for protecting the organs in a donor before and during removal, for protecting removed organs, for example when they are being treated with, or stored in, physiological bathing fluids, and also when transferring the organs into the recipient. The compounds are likewise valuable pharmaceuticals, having a protective effect, for use when carrying out angioplastic surgical interventions, for example on the heart or on peripheral blood vessels. In conformity with their protective effect against ischemically induced damage, the compounds are also suitable for use as pharmaceuticals for treating ischemias of the nervous system, in particular the CNS, where they are suitable, for example, for treating stroke or cerebral edema. In addition to this, the novel compounds of the formula I are also suitable for treating forms of shock, for example allergic, cardiogenic, hypovolemic and bacterial shock.

In addition to this, the novel compounds of the formula I are notable for their powerful inhibitory effect on the proliferation of cells, for example fibroblast cell proliferation and proliferation of the smooth muscle cells of the blood vessels. For this reason, the compounds of the formula I are suitable, as valuable therapeutic agents, for use in diseases in which cell proliferation constitutes a primary or secondary cause, and can therefore be used as antiatherosclerotics and as agents against late complications in diabetes, cancerous diseases, fibrotic diseases, such as pulmonary fibrosis, hepatic fibrosis or renal fibrosis, and organ hypertrophies and hyperplasias, in particular in association with hyperplasia or hypertrophy of the prostate.

The novel compounds are effective inhibitors of the cellular sodium/proton antiporter ($Na^+/H^+$ exchanger), which, in many diseases (essential hypertension, atherosclerosis, diabetes, etc.), is also elevated in cells which are readily accessible to measurement, for example in erythrocytes, thrombocytes or leukocytes. The novel compounds are therefore suitable for employment as simple and outstandingly good scientific tools, for example in their use as diagnostic agents for identifying and differentiating particular forms of hypertension and also atherosclerosis, diabetes, proliferative diseases, etc. In addition to this, the compounds of the formula I are suitable for use in preventive therapy for preventing the genesis of high blood pressure, for example essential hypertension.

In this context, pharmaceuticals which comprise a compound I may be administered orally, parenterally, intravenously or rectally, or by inhalation, with the preferred mode of administration depending on the particular clinical picture of the disease. In this context, the compounds I can be used either alone or together with pharmaceutical auxiliary substances, and be used both in veterinary medicine and in human medicine.

Based on his specialist knowledge, the skilled person is familiar with the auxiliary substances which are suitable for the desired pharmaceutical formulation. For example, antioxidants, dispersants, emulsifiers, defoamers, taste corrigents, preservatives, solubilizers or dyes can be used in addition to solvents, gelatinizing agents, suppository bases, tablet auxiliary substances and other active compound excipients.

For an oral use form, the active compounds are mixed with the additives, such as carrier substances, stabilizers or inert diluents, which are suitable for this purpose, and brought, using the customary methods, into the forms, such as tablets, coated tablets, hard gelatin capsules and aqueous, alcoholic or oily solutions, which are suitable for administration. Gum arabic, magnesium hydroxide, magnesium carbonate, potassium phosphate, lactose, glucose or starch, in particular corn starch, can, for example, be used as inert excipients. In this context, the preparation can be effected either as a dry granulate or as a wet granulate. Examples of suitable oily carrier substances or solvents are vegetable or animal oils such as sunflower oil or cod liver oil.

For subcutaneous or intravenous administration, the active compounds, if desired together with the substances which are customary for this purpose, such as solubilizers, emulsifiers or other auxiliary substances, are brought into solution, suspension or emulsion. Examples of suitable solvents are water, physiological sodium chloride solution or alcohols, for example ethanol, propanol and glycerol, and, in addition, sugar solutions, such as glucose solutions or mannitol solutions, or else a mixture of the different solvents mentioned.

Solutions, suspensions or emulsions of the active compound of the formula I in a pharmaceutically harmless solvent, such as, in particular, ethanol or water, or a mixture of these solvents, are suitable, for example, for use as a pharmaceutical formulation for administration in the form of aerosols or sprays.

If required, the formulation can also comprise other pharmaceutical auxiliary substances, such as surfactants, emulsifiers and stabilizers, and also a propellant gas. Such a preparation customarily comprises the active compound in a concentration of from about 0.1 to 10, in particular of from about 0.3 to 3% by weight.

The dose of the active compound of the formula I to be administered, and the frequency of administration, depend on the strength and duration of the action of the compounds used; they also depend on the nature and severity of the disease to be treated and on the sex, age, weight and individual responsiveness of the mammalian subject to be treated.

On average, the daily dose of a compound of the formula I is, in the case of a patient weighing approximately 75 kg, at least 0.001 mg/kg, preferably 0.01 mg/kg up to at most 10 mg/kg, preferably 1 mg/kg, of body weight. In the case of acute attacks of the disease, for example immediately after suffering a cardiac infarction, even higher, and in particular more frequent, doses may be necessary, for example up to 4 individual doses per day. In the case of i.v. use, in particular, up to 200 mg per day may be necessary, for example in the case of an infarction patient in intensive care.

List of abbreviations:

MeOH methanol

NMP N-methyl-2-pyrrolidinone

RT room temperature

EA ethyl acetate (EtOAc)

m.p. melting point

THF tetrahydrofuran

Experimental part

General protocol for preparing benzoylguanidines (I) from alkyl benzoates (II, L=O-alkyl)

1.0 eq. of the alkyl benzoate of the formula II and 5.0 eq. of guanidine (free base) are dissolved in isopropanol, or suspended in THF, and heated to boiling until reaction is complete (monitoring by thin layer chromatography) (typical reaction time, from 2 to 5 h). The solvent is distilled off under reduced pressure (in a rotary evaporator), and the residue is taken up in EA and this solution is washed 3× with $NaHCO_3$ solution. The EA solution is dried over $Na_2SO_4$, the solvent is distilled off in vacuo and the residue is chromatographed on silica gel using a suitable eluent, for example EA/MeOH 5:1.

EXAMPLE 1

2-Chloro4-methoxy-5-trifluoromethylbenzoylguanidine hydrochloride:

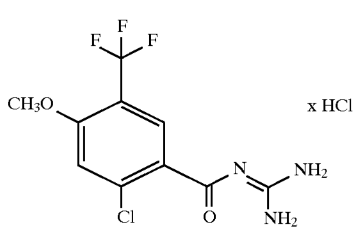

Colorless crystals, m.p. 232° C.

Synthesis route:

a) Methyl 2-chloro-5-iodo4-methoxybenzoate from methyl 2-chloro4-methoxybenzoate by reaction, at RT for 1 h, with 1.1 equivalents of N-chlorosuccinimide in the presence of 2 equivalents of potassium iodide in acetic acid; yellowish crystals, m.p. 120° C.

b) Methyl 2-chloro4-methoxy-5-trifluoromethylbenzoate from a) by heating to 90° C. with potassium trifluoroacetate in NMP in the presence of copper(l) iodide;

colorless crystals, m.p. 112° C.

c) 2-Chloro4-methoxy-5-trifluoromethylbenzoylguanidine hydrochloride from b) in accordance with the general protocol.

EXAMPLE 2

2-Chloro-3-iodo-5-trifluoromethylbenzoylguanidine hydrochloride: Colorless crystals, m.p. 268° C.

Synthesis route:

a) Methyl 2-chloro-3-iodo-5-trifluoromethylbenzoate from methyl 2-chloro-5-trifluoromethylbenzoate by reaction, at RT for 24 h, with 1 equivalent of N-iodosuccinimide in 5 equivalents of trifluoromethanesuifonic acid; colorless oil, $(M+H)^+=365$ b) 2-Chloro-3-iodo-5-trifluoromethylbenzoylguanidine hydrochloride from a) in accordance with the general protocol.

EXAMPLE 3

2-Chloro-3-methyl-5-trifluoromethylbenzoylguanidine hydrochloride: Colorless crystals, m.p. 236° C.

Synthesis route:

a) Methyl 2-chloro-3-methyl-5-trifluoromethylbenzoate from 2 a) by means of cross-coupling with 1.5 equivalents of methylzinc chloride (from methylmagnesium chloride by means of transmetallation with zinc(II) chloride etherate in THF) by stirring at RT in the presence of catal. palladium(II) [1,1'-bis(diphenylphosphino)ferrocene] chloride and copper(l) iodide, aqueous working-up, extraction with ethyl acetate and subsequent column chromatography on silica gel using ethyl acetate/n-heptane (3:7); colorless oil, $(M+H)^{+-}253$ b) 2-Chloro-3-methyl-5-trifluoromethylbenzoylguanidine hydrochloride from a) in accordance with the general protocol.

EXAMPLE 4

2-Chloro-3-n-propyl-5-trifluoromethylbenzoylguanidine hydrochloride: Colorless crystals, m.p. 208° C.

Synthesis route:

a) Methyl 2-chloro-3-n-propyl-5-trifluoromethylbenzoate from 2 a) by means of cross-coupling with 1.5 equivalents of n-propylzinc chloride as described under 3 a); colorless oil, $(M+H)^+=281$ b) 2-Chloro-3-n-propyl-5-trifluoromethylbenzoylguanidine hydrochloride from a) in accordance with the general protocol.

EXAMPLE 5

2-Chloro-3-isopropyl-5-trifluoromethylbenzoylguanidine hydrochloride: Colorless crystals, m.p. 183° C.

Synthesis route:

a) Methyl 2-chloro-3-isopropyl-5-trifluoromethylbenzoate from 2 a) by means of cross-coupling with 1.5 equivalents of isopropylzinc chloride, as described under 3 a);

colorless oil, $(M+H)^+=281$ b) 2-Chloro-3-isopropyl-5-trifluoromethylbenzoylguanidine hydrochloride from a) in accordance with the general protocol.

EXAMPLE 6

2-Chloro-3-cyclopentyl-5-trifluoromethylbenzoylguanidine hydrochloride:

Colorless crystals, m.p. 160° C.

Synthesis route:

a) Methyl 2-chloro-3-cyclopentyl-5-trifluoromethylbenzoate from 2 a) by means of cross-coupling with 1.5 equivalents of cyclopentylzinc chloride, as described under 3 a);

colorless oil, $(M+H)^+=307$ b) 2-Chloro-3-cyclopentyl-5-trifluoromethylbenzoylguanidine hydrochloride from a) in accordance with the general protocol.

EXAMPLE 7

2-Chloro4-cyclopentyl-5-trifluoromethylbenzoylguanidine hydrochloride: Colorless crystals, m.p. 245° C.

Synthesis route:

a) Methyl 2-chloro-4-cyclopentylbenzoate from methyl 2-chloro-4-bromobenzoate by means of cross-coupling with 1.5 equivalents of cyclopentylzinc chloride, as described under 3 a);

colorless oil, $(M+H)^+=238$ b) Methyl 2-chloro4-cyclopentyl-5-iodobenzoate from 7 a) by reaction at, RT for 24 h, with 1 equivalent of N-iodosuccinimide in 5 equivalents of trifluoromethanesulfonic acid;

colorless oil, $(M+H)^+=364$ c) Methyl 2-chloro4-cyclopentyl-5-trifluoromethyl benzoate from 7 b) by heating, at 90° C., with potassium trifluoroacetate in NMP in the presence of copper(l) iodide in analogy with 1 b);

colorless oil, $(M+H)^+=306$ d) 2-Chloro-4-cyclopentyl-5-trifluoromethyibenzoylguanidine hydrochloride from 7 c) in accordance with the general protocol.

EXAMPLE 8

2-Chloro4-n-propyl-5-trifluoromethylbenzoylguanidine hydrochloride:

Colorless crystals, m.p. 213° C.

Synthesis route:

a) Methyl 2-chloro-4-n-propylbenzoate from methyl 2-chloro4-bromobenzoate by means of cross-coupling with 1.5 equivalents of n-propylzinc chloride, as described under 3 a);

colorless oil, $(M+H)^+=212$ b) Methyl 2-chloro-4-n-propyl-5-iodobenzoate from 8 a) by reaction, at RT for 24 h, with 1 equivalent of N-iodosuccinimide in 5 equivalents of trifluoromethanesulfonic acid;

colorless oil, $(M+H)^+=338$ c) Methyl 2-chloro4-n-propyl-5-trifluoromethylbenzoate from 8 b) by heating, at 90° C., with potassium trifluoroacetate in NMP in the presence of copper(l) iodide, in analogy with 1 b);

colorless oil, $(M+H)^+=280$ d) 2-Chloro4-n-propyl-5-trifluoromethylbenzoylguanidine hydrochloride from 8 c) in accordance with the general protocol.

Pharmacological data:

Inhibition of the rabbit erythrocyte $Na^+/H^+$ exchanger

New Zealand White rabbits (Ivanovas) were given a standard diet containing 2% cholesterol for six weeks in order to activate $Na^+/H^+$ exchange and thereby making it possible to use flame photometry to determine the Na+influx into the erythrocytes by way of $Na^+/H^+$exchange. The blood was withdrawn from the aural arteries and rendered incoagulable by adding 25 IU of potassium heparin. A part of each sample was used for determining the hematocrit in duplicate by means of centrifugation. Aliquots of in each case 100 µl were used for measuring the initial content of $Na^+$ in the erythrocytes.

In order to determine the amiloride-sensitive sodium influx, 100 µl of each blood sample were in each case incubated, at 37° C. and pH 7.4, in 5 ml of a hyper osmolar salt/sucrose medium (mmol/l: 140 NaCl, 3 KCL, 150 sucrose, 0.1 ouabain, 20 tris(hydroxymethyl) aminomethane). After that, the erythrocytes were washed three times with an ice-cold MgCl$_2$/ouabain solution (mmol/l: 112 MgCl$_2$, 0.1 ouabain) and hemolyzed in 2.0 ml of distilled water. The intracellular content of sodium was determined by flame photometry.

The net Na$^+$influx was calculated from the difference between the initial sodium values and the sodium content of the erythrocytes after incubation. The amiloride-inhibitable sodium influx was obtained from the difference in the sodium content of the erythrocytes after incubating them with and without $3\times10^4$ mol/l amiloride. This procedure was also used in the case of the novel compounds.

Results

Inhibition of the Na$^+$/H$^+$ exchanger:

| Example | IC$_{50}$ (mol/l) |
|---------|-------------------|
| 1: | $0.02 \times 10^{-6}$ |
| 2: | $0.05 \times 10^{-6}$ |
| 4: | $0.07 \times 10^{-6}$ |
| 5: | $0.02 \times 10^{-6}$ |
| 6: | $0.06 \times 10^{-6}$ |
| 7: | $0.03 \times 10^{-6}$ |
| 8: | $0.01 \times 10^{-6}$ |

| Example | Intraduodenal bioavailability | Plasma elimination: Half life |
|---------|-------------------------------|-------------------------------|
| 5 | good | Rat, i.V. 0.7 h |
| 1 | good | Dog, i.V. 1.1 h |
|   |      | Rat, i.V. 0.32 h |

We claim:

1. An ortho-substituted benzoylguanidine of the formula I

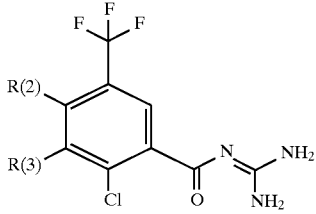

in which:

R(2) and R(3) are,
independently of each other, hydrogen, Cl, Br, l, (C$_1$–C$_8$)-alkyl, (C$_3$–C$_8$)-cycloalkyl or —OR(5);
R(5) is (C$_1$–C$_8$)-alkyl or —C$_d$H$_{2d}$—(C$_3$–C$_8$)-cycloalkyl;
d is zero, 1 or 2;
where one of the two substituents R(2) and R(3) is always hydrogen but both substituents R(2) and R(3) are not simultaneously hydrogen, and the pharmaceutically tolerated salts thereof.

2. A compound of the formula I as claimed in claim 1, in which:

R(2) and R(3) are,
independently of each other, hydrogen, Cl, Br, l, (C$_1$–C$_8$)-alkyl, (C$_3$–C$_8$)-cycloalkyl or —OR(5);
R(5) is (C$_1$–C$_8$)-alkyl;
and the pharmaceutically tolerated salts thereof.

3. A compound of the formula I as claimed in claim 1, which is selected from the group consisting of:
2-chloro4-methoxy-5-trifluoromethylbenzoylguanidine hydrochloride, 2-chloro-3-methoxy-5-trifluoromethylbenzoylguanidine hydrochloride, 2-chloro-3-iodo-5-trifluoromethylbenzoylguanidine hydrochloride, 2-chloro-3-methyl-5-trifluoromethylbenzoylguanidine hydrochloride, 2-chloro-3-n-propyl-5-trifluoromethylbenzoylguanidine hydrochloride, 2-chloro-3-isopropyl-5-trifluoromethylbenzoylguanidine hydrochloride, 2-chloro-3-tert-butyl-5-trifluoromethylbenzoylguanidine hydrochloride, 2-chloro-3-cyclopentyl-5-trifluoromethylbenzoylguanidine hydrochloride, 2-chloro4-methyl-5-trifluoromethylbenzoylguanidine hydrochloride, 2-chloro4-n-propyl-5-trifluoromethylbenzoylguanidine hydrochloride, 2-chloro-4-isopropyl-5-trifluoromethylbenzoylguanidine hydrochloride, 2-chloro4-tert-butyl-5-trifluoromethylbenzoylguanidine hydrochloride and 2-chloro-4-cyclopentyl-5-trifluoromethylbenzoylguanidine hydrochloride.

4. A process for preparing a compound of the formula I as claimed in claim 1, which comprises reacting a compound of the formula II

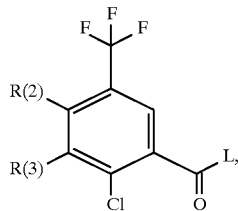

in which R(2) and R(3) have the given meaning and L is a leaving group which can readily be substituted nucleophilically, with guanidine.

5. A method for the treatment or prophylaxis of disease which are brought about by isochemic conditions, comprising administering to a patient in need of said treatment or prophylaxis an effective amount of a compound of claim 1.

6. A method for the treatment or prophylaxis of cardiac infarction, comprising administering to a patient in need of said treatment or prophylaxis an effective amount of a compound of claim 1.

7. A method for the treatment or prophylaxis of angina pectoris comprising administering to a patient in need of said treatment or prophylaxis an effective amount of a compound of claim 1.

8. A method for the treatment or prophylaxis of ischemic conditions of the heart, comprising administering to a patient in need of said treatment or prophylaxis an effective amount of a compound of claim 1.

9. A method for the treatment or prophylaxis of ischemic conditions of the peripheral and central nervous system and of stroke, comprising administering to a patient in need of said treatment an effective amount of a compound of claim 1.

10. A method for the treatment or prophylaxis of ischemic states of peripheral organs and limbs, comprising administering to a patient in need of said treatment an effective amount of a compound of claim 1.

11. A method for the treatment of shock conditions, comprising administering to a patient in need of said treatment an effective amount of a compound of claim 1.

12. A pharmaceutical composition for administration to patients undergoing surgical operations and organ transplantations, comprising an effective amount of a compound of claim 1 together with a pharmaceutically acceptable carrier.

13. A method for the preservation and storage of transplants for surgical procedures, comprising treating said transplants with an effective amount of a compound of claim 1.

14. A method for the treatment of diseases in which cell proliferation constitutes a primary or secondary cause, comprising administering to a patient in need of said treatment an effective amount of a compound of claim 1.

15. A pharmaceutical composition comprising a compound of the formula I as claimed in claim 1 together with a pharmaceutically acceptable carrier.

16. A method for treating atherosclerosis, late diabetic complications, cancerous diseases, fibrotic diseases, or prostate hyperplasia, comprising administering to a patient in need of said treatment an effective amount of a compound of claim 1.

17. The method according to claim 16, wherein said fibrotic diseases are pulmonary fibrosis, hepatic fibrosis or renal fibrosis.

18. The composition of claim 15, wherein the compound of claim 1 is present in an amount effective to treat arrhythmias, cardiac infarctions, angina pectoris, ischemic states of the heart, ischemic states of the peripheral and central nervous system and the apoplexy, ischemic states of peripheral organs and limbs or states of shock.

* * * * *

UNITED STATES PATENT AND TRADEMARK OFFICE
CERTIFICATE OF CORRECTION

PATENT NO. : 5,856,574
DATED : January 05, 1999
INVENTOR(S) : Andreas Weichert et al.

It is certified that error appears in the above-identified patent and that said Letters Patent is hereby corrected as shown below:

column 1, line 25 "1" should read --I--.

Claim 1, column 9, line 48 "1" should read --I--.

Claim 2, column 9, line 59 "1" should read --I--.

Claim 3, column 9, line 65 and column 10, lines 12 and 15, "chloro4" should read --chloro-4--.

Signed and Sealed this

Sixteenth Day of November, 1999

Attest:

Q. TODD DICKINSON

Attesting Officer     Acting Commissioner of Patents and Trademarks